(12) United States Patent
Morgan

(10) Patent No.: US 10,342,951 B2
(45) Date of Patent: Jul. 9, 2019

(54) BONDING SYSTEM FOR BALLOON MESH AND OTHER STRUCTURES

(71) Applicant: Roy E. Morgan, Alameda, CA (US)

(72) Inventor: Roy E. Morgan, Alameda, CA (US)

(73) Assignee: Sanovas Intellectual Property, LLC, Reno, NV (US)

(*) Notice: Subject to any disclaimer, the term of this patent is extended or adjusted under 35 U.S.C. 154(b) by 72 days.

(21) Appl. No.: 15/099,196

(22) Filed: Apr. 14, 2016

(65) Prior Publication Data

US 2016/0303841 A1   Oct. 20, 2016

Related U.S. Application Data

(60) Provisional application No. 62/147,290, filed on Apr. 14, 2015.

(51) Int. Cl.
*A61M 25/00* (2006.01)
*B32B 27/32* (2006.01)
*B29C 63/18* (2006.01)

(52) U.S. Cl.
CPC ......... *A61M 25/0009* (2013.01); *B29C 63/18* (2013.01); *B32B 27/32* (2013.01)

(58) Field of Classification Search
CPC ....... B32B 37/144; B32B 27/32; B29C 61/02; B29C 61/0226; B29C 65/66; B29C 66/73715; B29C 63/18; A61M 25/0009; A61M 25/1011; A61M 25/1027; A61M 25/1034; B29K 2995/0049; H01R 4/72; B65C 3/06; B65C 3/065

USPC ............ 604/101.01, 101.02, 101.03, 101.04, 604/101.05, 919

See application file for complete search history.

(56) References Cited

U.S. PATENT DOCUMENTS

| | | | | | |
|---|---|---|---|---|---|
| 3,316,343 | A | * | 4/1967 | Sherlock | B29C 61/0616 174/84 R |
| 3,896,067 | A | * | 7/1975 | Kosaka | C08F 255/00 524/465 |
| 4,198,119 | A | * | 4/1980 | Uberbacher | G02B 6/245 264/1.25 |
| 5,190,058 | A | * | 3/1993 | Jones | A61F 2/90 128/898 |
| 6,447,479 | B1 | * | 9/2002 | Nobuyoshi | A61M 25/104 604/921 |
| 7,678,223 | B2 | * | 3/2010 | Strong | A61M 25/0009 156/158 |
| 2008/0271832 | A1 | * | 11/2008 | Pieslak | B29C 61/0616 156/85 |
| 2013/0225962 | A1 | * | 8/2013 | Saleh | A61B 5/065 600/373 |

\* cited by examiner

*Primary Examiner* — John L Goff, II
(74) *Attorney, Agent, or Firm* — Forge IP, PLLC

(57) ABSTRACT

A system and method for bonding a porous structure to at least one other structure is provided, including an inner adhesive member adapted to be positioned adjacent the porous structure and having a melting temperature, and an outer shrink wrap member positioned over and at least partially enclosing the inner adhesive member, the outer shrink wrap member having a recovery temperature, wherein the melting temperature is higher than the recovery temperature.

13 Claims, 3 Drawing Sheets

BONDING SYSTEM FOR BALLOON MESH AND OTHER STRUCTURES

FIELD OF THE INVENTION

The disclosed invention relates to bonding systems utilizing heat-shrinkable polymers and hot-melt adhesives. More specifically, the invention relates to a system and method for bonding a porous structure to at least one other structure, wherein the bonding systems is a combination of an inner flowable adhesive member with an outer heat-shrinkable member such that, when paired in the un-recovered state, the two members form a stable mechanical construct that can be easily fit over two independent cylindrical members of flexible or rigid material that have porous surfaces.

BACKGROUND OF THE INVENTION

Bonding systems for various types of materials are widely used in different industries. Some of the commonly used methods of bonding various materials together is by use of hot-melt type adhesives. Such hot-melt adhesives are typically applied by means of a hot-gun type device. One of the drawbacks associated with this bonding method is a so-called web/thread formation at the point where traditional hot-melt adhesives are being dispensed. In other words, when the hot-melt adhesive is stopped being dispensed, it will begin to solidify creating a "web" or "thread" that pulls away from the substrate being bonded. This creates both cleanliness and cosmetic issues that are undesirable for various applications.

One of the areas where the bonding systems are commonly used is the field of balloon catheters. The balloon catheters are used for a variety of medical procedures in urology, cardiology, surgery, etc. One of the common ways of attaching a balloon to a catheter shaft and/or for attaching an external woven structure or mesh to the balloon wall is my means of tying the ends of the balloon/mesh with a fiber string, some type of a wrap material or any other similar mechanism. The disadvantage of such bonding approach is that it creates bulky areas at the point of attachment that have a substantially larger diameter than the diameter of the catheter shaft and/or the balloon in its deflated state. This is undesirable for most medical applications, and in particular, for procedures where a balloon catheter needs to be inserted into small bodily cavities and passageways.

Another way of bonding the balloon to the catheter shaft and/or to the mesh is by means of a hot-melt adhesive applied via a hot-gun device to the attachment points. As described above, this approach results in creation of solidified adhesive web/threads and thus, presents issues with cleanliness of the device that require further manufacturing steps to fix. Another problem with this approach is that the hot-melt adhesive may spread to the areas of the balloon and/or mesh where it is undesirable to have the solidified adhesive because it may interfere with the function of the device (e.g., balloon inflation or shape). In order to fix this issue, additional steps of removing the solidified adhesive may be necessary. Removal of excess adhesive from the perimeter of the finished structure with sharps presents severe danger to the integrity of the materials of construction that could result in catastrophic damage to the finished device and, more specifically, to the pneumatic integrity of the balloon.

Accordingly, it is an objective of the present invention to provide a system and method for bonding materials together, and in particular, bonding various layers of a balloon catheter and simultaneously eliminating the steps of adhesive shaping and removal, that overcomes the disadvantages of the prior art methods and systems described above. It is also an objective of the present invention to provide a bonding system that provides for a uniform pressure-flow of hot-melt adhesive and simultaneous containment of the adhesive that solves the adhesive web/thread formation described above. It is further an objective of the present invention to provide a bonding system that ensures that only the areas desired to be covered by the adhesive (adhesive lay-down and shaping) are controlled more effectively than by means of traditional hot-gun application of hot-melt adhesives. It is yet another objective of the present invention to provide a bonding system that creates a very low profile and at the same time very durable bonding mechanism.

SUMMARY OF THE INVENTION

In order to overcome the deficiencies of the prior art and to achieve at least some of the objects and advantages listed, the invention comprises a system for bonding a porous structure to at least one other structure, including an inner adhesive member adapted to be positioned adjacent the porous structure and having a preferential melting temperature, and an outer shrink wrap member positioned over and at least partially enclosing the inner adhesive member, the outer shrink wrap member having a recovery temperature, wherein the melting temperature is higher than the recovery temperature.

In some embodiments, the melting temperature is higher than the recovery temperature by at least about ten degrees Fahrenheit.

In certain embodiments, the inner adhesive member comprises a maleic anhydride modified ethylene-vinyl acetate copolymer, such as that produced by Arkema, Corp. of Pennsylvania. In additional embodiments, the inner adhesive member comprises a linear low-density polyethylene adhesive resin or a high-density polyethylene adhesive resin. In further embodiments, the outer shrink wrap member comprises a polyolefin. In yet further embodiments, the outer shrink wrap member comprises a polyethylene.

In some cases, the outer shrink wrap member has at least one weakened zone such that the outer shrink wrap member is adapted to be torn along the weakened zone and removed after the bonding process is completed.

In certain embodiments, the outer shrink wrap member exerts pressure on the inner adhesive member upon reaching the recovery temperature such that the adhesive member disperses inward radially and minimally outwardly along the long-axis of contraction, and into voids in the porous structure.

In some embodiments, the inner adhesive member is at least partially fixated inside the outer shrink wrap member prior to positioning the inner adhesive member adjacent the porous structure.

In certain embodiments, the inner adhesive member has a cylindrical shape with an outer diameter. In some of these embodiments, the outer shrink wrap member has a cylindrical shape with an inner diameter that is slightly larger than the outer diameter of the inner adhesive member such that the inner member is accommodated inside the outer member.

In some embodiments, the bonding system is applied to a catheter with an inflatable balloon positioned at a distal end of the catheter, and a mesh structure positioned over at least a portion of the inflatable balloon, wherein the inner diameter of the inner adhesive member is positioned adjacent the mesh structure. In certain of these embodiments, the outer shrink wrap member exerts pressure on the inner adhesive member upon reaching the recovery temperature such that the inner adhesive member disperses inward radially and minimally outwardly along the long-axis of contraction, and into voids in the mesh structure to bond the mesh structure to the inflatable balloon. In some of these embodiments, the inner adhesive member simultaneously comes into contact with an elongated shaft of the catheter during the recovery step and bonds the mesh structure and the inflatable balloon to the elongated shaft.

In certain embodiments, the catheter has a first inflatable balloon positioned at the distal end of the catheter and having a mesh structure positioned over at least a portion of the first balloon and a second inflatable balloon positioned proximally of the first balloon and having a mesh structure positioned over at least a portion of the second balloon, wherein the inner adhesive member is positioned over at least a portion of the first balloon mesh structure and at least a portion of the second balloon mesh structure. In some of these embodiments, upon reaching the melting temperature, the inner adhesive member disperses into voids in the mesh structure of the first and second balloons to bond the mesh structure to the first and second balloons.

In present invention further comprises a method for bonding a porous material to another material, including the steps of positioning an inner adhesive member adjacent the porous material, the inner adhesive member having a preferential melting temperature, positioning an outer shrink wrap member over the inner adhesive member to at least partially enclose said inner adhesive member, the outer shrink wrap member having a recovery temperature, wherein the recovery temperature is lower than the melting temperature of the inner adhesive member, exposing the outer shrink wrap member to a temperature that is at least equal to the recovery temperature to cause the outer shrink member to contract around the inner adhesive member, and exposing the inner adhesive member to a temperature that is at least equal to the melting temperature to cause the inner adhesive member to disperse into voids in the porous material and bond the porous material to another material.

In some embodiments, the step of exposing the outer shrink wrap member to the temperature that is at least equal to the recovery temperature causes the outer shrink member to exert pressure on the inner adhesive member such that the inner member disperses inward radially and minimally outwardly along the long-axis of contraction.

In certain embodiments, the method further includes the step of removing the outer shrink wrap member after completion of the bonding step.

In some cases, the method also includes the step of at least partially fixating the inner adhesive member to the outer shrink wrap member prior to the step of positioning the inner adhesive member adjacent the porous material by exposing the outer member to a temperature that is at least equal to the recovery temperature but is less than the melting temperature to cause the outer member to partially contract around the inner member sufficient to hold it in place.

In certain embodiments, the bonding step creates a composite structure comprising the inner adhesive member, the porous material and another material. In some of these embodiments, fully recovered and impregnated surface of the composite structure is formed that is substantially flush with a surface of the porous material.

In some embodiments, the melting temperature is higher than the recovery temperature by at least about ten degrees Fahrenheit.

In certain embodiments, the inner adhesive member comprises a maleic anhydride modified ethylene-vinyl acetate copolymer, such as that produced by Arkema, Corp. of Pennsylvania. In additional embodiments, the inner adhesive member comprises a linear low-density polyethylene adhesive resin or a high-density polyethylene adhesive resin. In further embodiments, the outer shrink wrap member comprises a polyolefin. In yet further embodiments, the outer shrink wrap member comprises a polyethylene.

Other objects of the invention and its particular features and advantages will become more apparent from consideration of the following drawings and accompanying detailed description.

DETAILED DESCRIPTION OF THE INVENTION

Figure 1A:
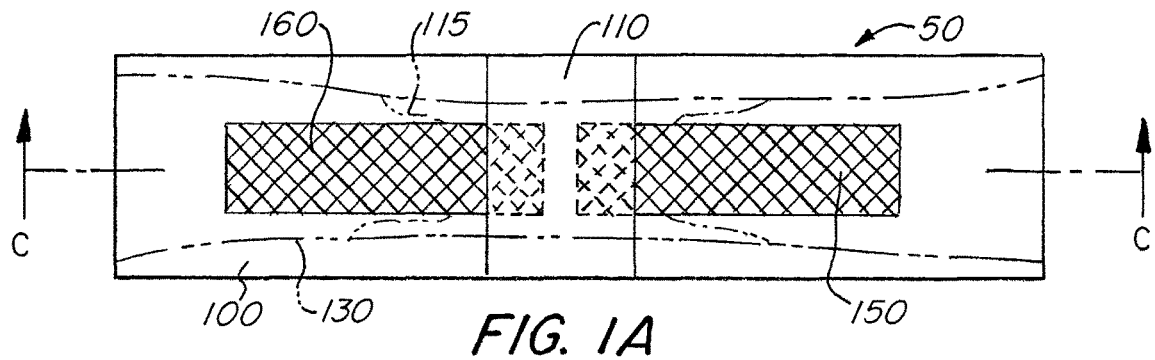
FIG. 1A is a schematic view of the bonding system in accordance with the present invention.

The basic components of an exemplary embodiment of a system for bonding a porous structure to another structure in accordance with the invention are illustrated in FIG. 1A. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1A, the system of the present invention is used to bond two porous materials/structures [160] and [150]. Those skilled in the art will recognize that the porous materials may include any open-cell type structures, knitted structures, mesh structures and the like. It is understood, however, that the system of the present invention is also utilized to bond a porous material/structure to any other type of material or structure that does not necessarily need to be porous.

Figure 1B:
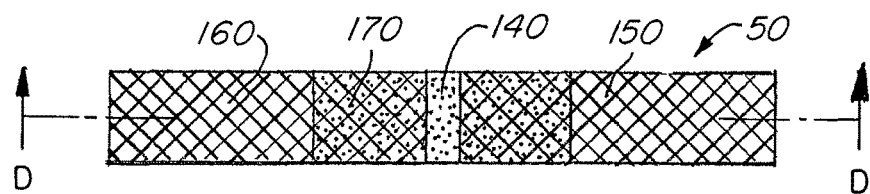
FIG. 1B is a schematic view of the bonding system of FIG. 1a, showing a composite structure formed by the bonding process.
Figure 1C:
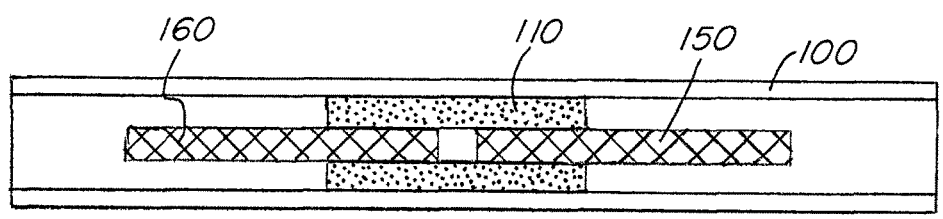
FIG. 1C is a cross-sectional view of the bonding system of FIG. 1a, taken along the line "C-C".

The bonding system [50] includes an inner adhesive member [110] and an outer shrink wrap member [100]. The inner adhesive member [110] is positioned over at least a portion of each of the two structures to be bonded together. As best shown in FIG. 1C, the inner member [110] is positioned over a portion of the mesh structure [150] and a portion of the mesh structure [160]. The outer shrink wrap member [100] is positioned over and at least partially encloses the inner adhesive member [110].

The inner member [110] is made with any suitable thermally stabilized/activated "hot-melt" adhesive type polymer that has a particular melting temperature. The outer shrink wrap member [100] is made with a suitable polymer that has a recovery temperature that is at least slightly lower than the melting temperature of the inner adhesive member. In some embodiments, the melting temperature is higher than the recovery temperature by at least about ten degrees Fahrenheit. Examples of suitable polymers for the inner member [110] and the outer member [100] include polyolefin and polyethylene polymers. In some preferred embodiments, the inner adhesive member [110] is made with a maleic anhydride modified ethylene-vinyl acetate copolymer, such as Orevac® sold by the Arkema, Corp. of Pennsylvania. In alternate preferred embodiments, the inner adhesive member [110] is made with a linear low-density polyethylene adhesive resin or a high-density polyethylene adhesive resin. In additional embodiments, the outer shrink member [100] is made with shrinkable PET or PVC.

It is understood that any other polymers may be used for their inner adhesive member [110] and the outer shrink wrap member [100] as long as they have appropriately paired melting and recovery temperatures.

As the bonding system [50] is exposed to a temperature that is at least equal to the recovery temperature of the outer shrink wrap member [100], the shrink wrap member [100] begins to contract, as shown by dashed lines [130] in FIG. 1A. At the same time, the inner adhesive member [110] reaches its glass-transition temperature and becomes pliable, though not necessarily flowable. As the temperature is increased on the overall structure, the inner adhesive member [110] reaches its melting temperature and achieves full flowability. It is simultaneously compressed through the compressive force exerted by the outer shrink wrap member [100] as it continues to contract.

As the compressive force increases toward the terminal shrunken state of the outer shrink wrap member [100], the inner adhesive member [110] flows inward radially towards the porous materials [150, 160] due to volumetric constraints created by the narrowing diameter/surface [130] of the outer shrink wrap member [100], as schematically shown by dashed lines [115] in FIG. 1A. This results in a flow of the heated adhesive [110] into the interstitial voids of the two porous materials [150,160], thereby forming a composite structure [170], as shown in FIG. 1B, while at the same time being contained within the outer shrink wrap member [100]. It is noted that some of the adhesive [110] may also flow outwardly along the long axis of contraction, but this outward flow is controlled and contained by the outer shrink wrap member [100].

After the inner adhesive member [110] has sufficiently spread out and impregnated the voids in the porous members [150,160] forming the composite structure [170], the structure is allowed to cool. The resulting composite structure [170] provides a very strong bond between the two porous material [150, 160]. It is understood that, where a substrate is also present with the porous materials, the inner adhesive member [110] may flow through the voids in the porous materials [150, 160] and to the substrate, providing a bond between the porous materials and the substrate, as described in more detail below.

Figure 1D:
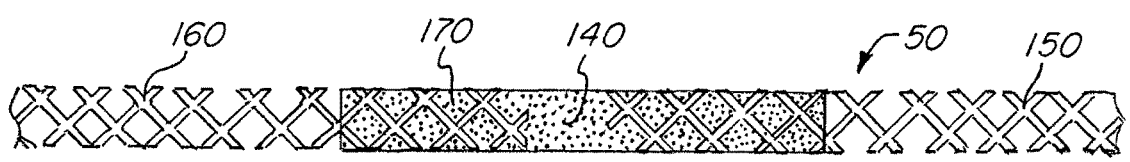
FIG. 1D is a cross-sectional view of the bonding system of FIG. 1b, taken along the line "D-D."

In some exemplary embodiments, when the outer shrink wrap member [100] is in its terminal shrunken state, the inner surface [130] of the outer member [100] is substantially flush with the outer surface of the porous member(s) [150,160]. Or alternatively, the outer shrink wrap member [100] is removed upon reaching its terminal shrunken state and after completion of the bonding process, and the outer surface of the resulting composite structure [170] is substantially flush with the outer surface of the porous member(s) [150,160], as shown in FIG. 1D. This is advantageous because it produces a very low profile bonding mechanism of attaching a porous material to another porous material and/or or a substrate, which is desirable in a number of applications, one example of which is described below.

It is also important to note that, dependent on the degree of mechanical pressure exerted by the outer shrink wrap member [100] to force the two porous materials [150,160] together, an additional benefit of this approach is that an adhesive bond is achieved to fill any gap [140] that may inadvertently exist between the two members [150,160], as shown in FIG. 1B.

After the bonding process is completed, the outer shrink wrap member [100] may be removed leaving only the inner adhesive member [110] and the two porous materials [150, 160] bonded together, as shown in FIGS. 1B and 1D. For example, the outer shrink wrap member [100] may be provided with at least one weakened zone, e.g. a perforated line, such that the outer member [100] can be torn along the weakened zone and removed once the bonding is completed and the materials are cooled down. This is possible because the materials used for the outer shrink wrap member [100] do not adhere to the inner adhesive member [110] and/or to the porous materials [150, 160] during the bonding process. The outer shrink wrap member [100] is thus being used only as a guide for the flowability of the inner adhesive member [110] during the process of dynamic shrinking to direct the mechanical motion of the adhesive flow allowing the flowing adhesive to take hold of the two porous materials [150, 160]. It is understood that the outer shrink wrap member [100] may be removed by any other method, such as simply cutting it away.

Figure 2A:
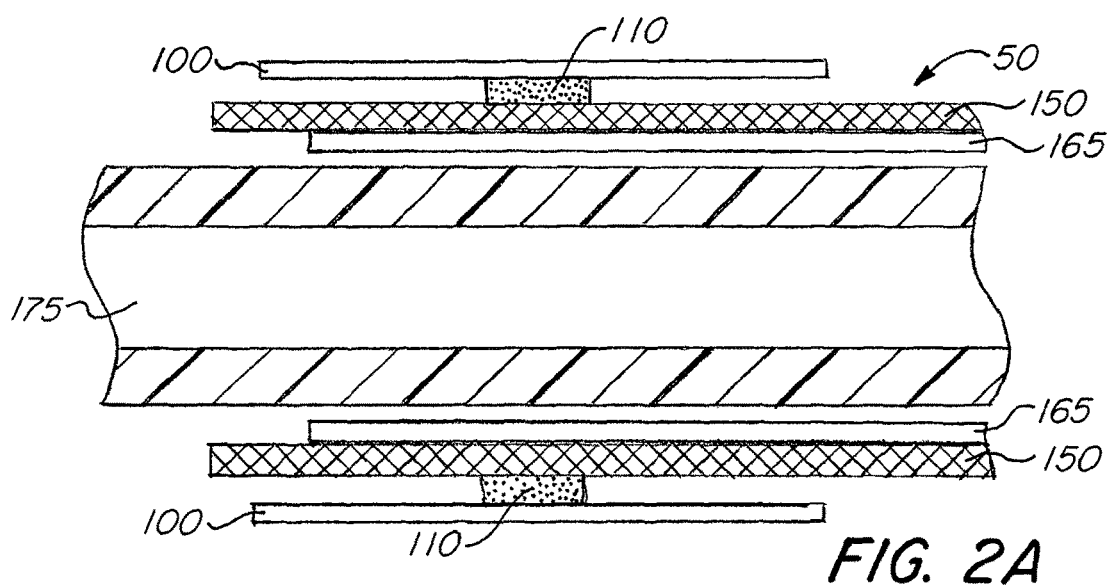
FIG. 2A is a cross-sectional partially schematic view of a distal end of a balloon catheter with the bonding system of the present invention.
Figure 2B:
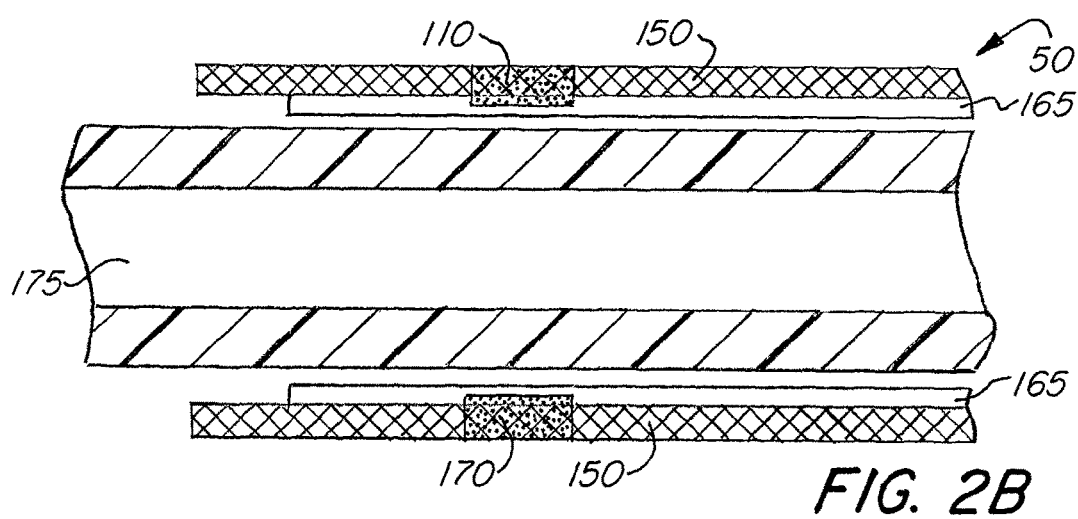
FIG. 2B is a cross-sectional partially schematic view of the distal end of the balloon catheter of FIG. 2A, showing a composite structure formed by the bonding process.
Figure 2C:
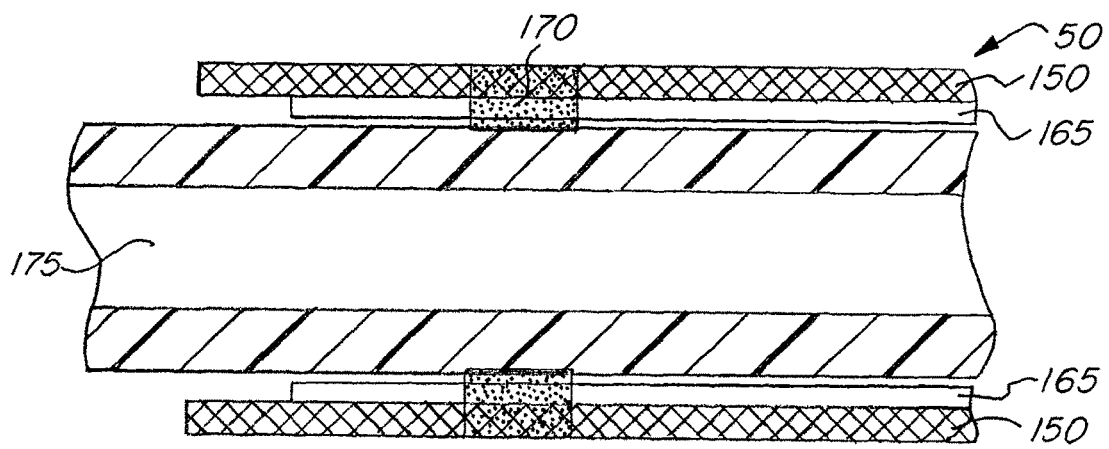
FIG. 2C is a cross-sectional partially schematic view of the distal end of the balloon catheter of FIG. 2A, showing a composite structure formed by the bonding process.

FIGS. 2A-2C describe an exemplary tubular construction of a porous material [150] using the bonding system [50] of the present invention. In particular, these figures illustrate a balloon catheter with an elongated shaft [175], an inflatable balloon [165] positioned at a distal end of the elongated catheter shaft and a mesh structure [150] positioned over at least a portion of the inflatable balloon. As shown in FIG. 2A, the bonding system [50] comprises an inner adhesive member [110] positioned adjacent the mesh structure and an outer shrink wrap member [100] positioned over and at least partially enclosing the inner member [110].

Once the bonding structure [50] is exposed to heat, the outer shrink wrap member [100] begins to contract inwardly around the inner adhesive member [110]. An increase in the temperature causes the inner adhesive member [110] to become more flowable and the narrowing inner diameter of the outer shrink wrap member [100] exerts dynamic pressure on the inner member [110] causing it to spread inward radially and minimally outwardly along the long-axis of contraction and into the voids in the mesh [150].

The continuing pressure of the outer member [100] causes the adhesive [110] to at least partially flow through the mesh [150] and make adhesive contact with the substrate material, in this case, a wall of the inflatable balloon [165]. This results in bonding of the mesh [150] to the balloon [165] by creating a composite structure [170], as shown in FIG. 2B.

It is also envisioned that the outer shrink wrap member [100] may continue to exert pressure on the inner adhesive member [110] such that the adhesive permeates the wall of the balloon [165] and makes an adhesive contact with the wall of the elongated shaft [175], creating a bonding structure [185] as shown in FIG. 2C, that bonds the balloon with the mesh to the catheter shaft. This provides a very strong and at the same time very simple bonding system for a balloon catheter with a mesh positioned over the balloon. Alternatively, the mesh structure [150] may extend beyond the ends of the balloon [165] such that it is in direct contact with the elongated shaft [175]. In this case, the inner adhesive member [110] flows through the voids in the mesh [150] and to the wall of the elongated shaft [175], thereby bonding the mesh directly to the shaft.

In an advantageous embodiment, the inner diameter of the outer shrink wrap member [100] when it is in its terminal shrunken state is substantially equal to the outer diameter of the mesh [150]. This way, the pressure exerted on the inner adhesive member [110] by the outer member [100] forces the adhesive into the voids in the mesh, such that the outer diameter of the composite structure [170, 185] created by the bonding process is substantially equal to the outer diameter of the mesh [150], as shown in FIGS. 2B and 2C. This creates a very low profile and at the same time very strong bonding mechanism for attaching a mesh to the balloon that does not add to the outer diameter of the catheter, which is very important for many medical procedures, especially when the catheter is inserted into very small bodily luminal structures and passages.

As described above, once the bonding process is completed and the composite structure is cooled down, the outer shrink wrap member [100] may be removed from the balloon catheter, as illustrated in FIGS. 2B and 2C, by tearing it along a weakened line, by cutting it away, or by any other suitable method.

It is understood that the substrate for the mesh material is not limited to the inflatable balloon [165], and may also include co-extrusion material, rigid metal banding, and/or additional porous flexible materials or knitted mesh materials. Those skilled in the art will recognize that the properties of the heat-shrinkable hot-melt bonding system of the present invention can perform multiple cylindrically concentrically located layers of bonding dependent on the amount and recovery diameter of the heat-shrinkable hot-melt system.

In an advantageous embodiment, the bonding system [50] of the present invention is used to secure a mesh to the balloon of a catheter, such as that disclosed in U.S. Pat. No. 8,226,601 to Gunday et al., and U.S. Pat. Nos. 8,597,239, 8,540,667, and 8,348,890 to Gerrans et al. In this way, the mesh can be securely affixed to both ends of the balloon, or alternatively, to the catheter adjacent each end of the balloon.

In order to affix the mesh [150] to the inflatable balloon [165] of the balloon catheter using the bonding system [50] of the present invention, the balloon [165] is first attached to the catheter shaft [175] by any suitable method. Then, the inner adhesive member [110], preferably in its solid state, is shaped into a cylinder that corresponds to the shape of the mesh [150]. The outer diameter of the cylindrical adhesive [110] is slightly smaller than the inner diameter of the outer shrink wrap member [100], which also has a cylindrical shape, such that the adhesive [110] fits inside the shrink wrap [100]. The solid adhesive [110] is slid into the outer shrink wrap member [100]. The mesh sleeve [150] is placed over the balloon [165] and the shrink wrap member [100] together with the adhesive [110] is slid over the balloon with the mesh such that it covers at least a portion of the balloon surface and the mesh surface. Next, the bonding system is exposed to a source of heat that causes the outer shrink wrap member [100] to begin contracting upon reaching its recovery temperature. Continued exposure to heat causes the adhesive to soften and ultimately become flowable upon reaching its melting temperature. The dynamic pressure exerted upon the adhesive [110] by the shrinking outer member [100] forces to adhesive to disperse inward radially and minimally outwardly along the long-axis of contraction and into the voids in the mesh [150]. At the same time, the outer member [100] helps to contain the adhesive [110] such that it does not spread too much and interfere with other parts of the mesh, balloons or the catheter shaft. Once the outer shrink wrap member [100] has reached it terminal shrunken state and the adhesive has spread out into and through the mesh and came into contact with the balloon wall, forming a composite bonding structure [170], the adhesive is allowed to cool down. After the bonding process is completed, the outer shrink wrap member [100] may be optionally removed from the composite structure [170].

In some embodiments, it may be desirable to affix the inner adhesive member [110] inside the outer shrink wrap member [100] prior to positioning the bonding system [50] over the balloon with the mesh. This makes the assembly and bonding process easier and more efficient. This may be achieved by prefixing the adhesive [110] inside the outer shrink wrap member [100] by exposing the outer member [100] to a temperature that it equal to or slightly above the recovery temperature of the outer member for a period of time substantially less than that required to achieve full recovery of the expanded shrink wrap member [100], and which, but is less than the melting temperature of the adhesive, such that the outer member [100] partially contracts around the adhesive [110] thereby fixating the adhesive inside the shrink wrap. The heat is applied to the outside of the shrink wrap member [100], and the heat energy is absorbed by the shrink wrap member, which acts as an insulator to the adhesive member, so that little to no heat is transmitted to the adhesive, thus preventing it from melting. Then, the adhesive/shrink wrap construct is positioned over the balloon mesh or any other desirable structure/material and further heat is applied to bond the structures together, as described above.

Figure 3A:
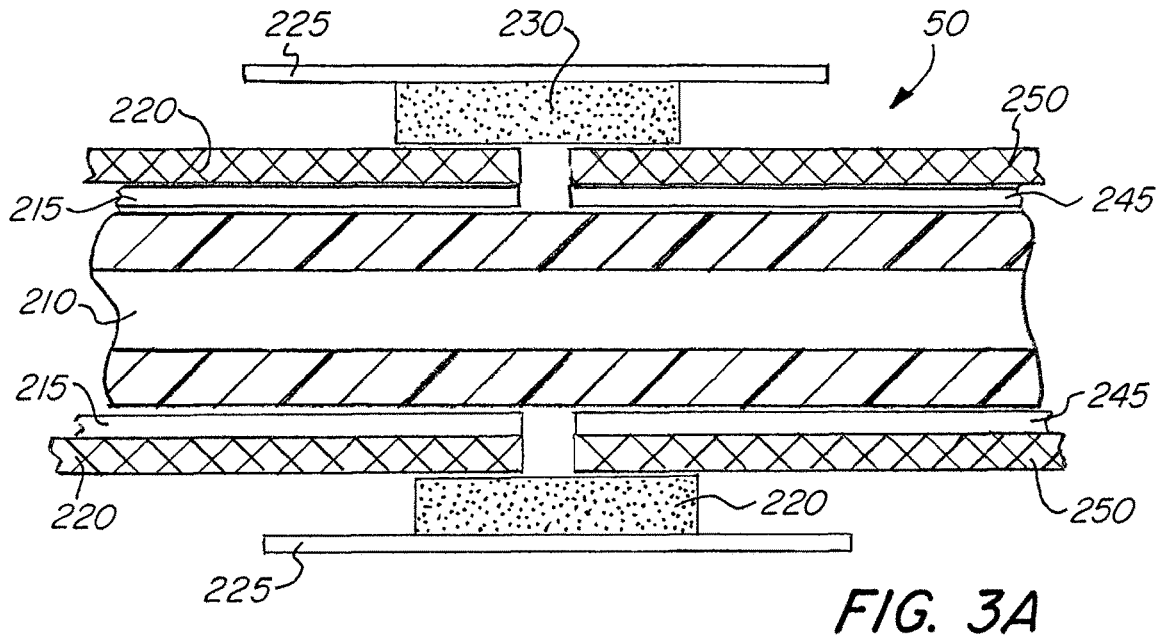
FIG. 3A is a cross-sectional partially schematic view of a distal end of a double balloon catheter with the bonding system of the present invention.
Figure 3B:
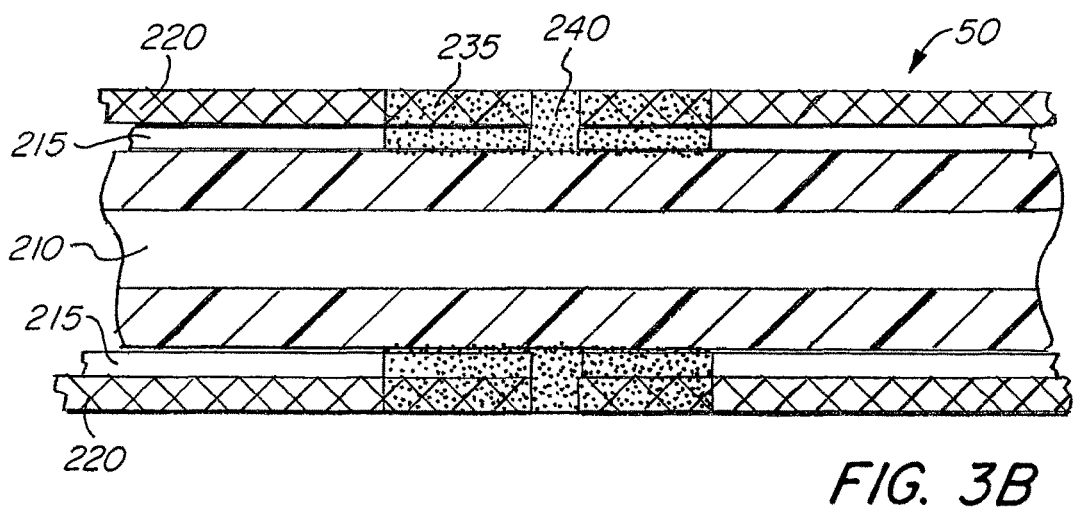
FIG. 3B is a cross-sectional partially schematic view of the distal end of the double balloon catheter of FIG. 2A, showing a composite structure formed by the bonding process.

FIGS. 3A and 3B illustrate another exemplary embodiment of the present invention, in which the bonding system of the present invention is used on a double balloon catheter. As shown in FIG. 3A, the catheter includes an elongated shaft [210] with a first balloon [215] positioned at a distal end of the shaft and a second balloon [245] positioned proximally from the first balloon. The first balloon [215] has a mesh structure [220] positioned over at least a portion of the balloon wall, and the second balloon [245] has a mesh structure [250] positioned over at least a portion of the balloon wall. A cylindrical inner adhesive member [230] is positioned over at least a portion of both mesh structures [220] and [250], and a cylindrical outer shrink wrap member [225] is positioned over and at least partially encloses the adhesive [230]. In an advantageous embodiment, as shown in FIG. 3A, the length of the outer shrink wrap member [225] is longer than the length of the inner adhesive member [230] such that the shrink wrap member extends past the adhesive member sufficiently to contain the adhesive member once it disperses inward radially and minimally outwardly along the long-axis of contraction, as shown in FIG. 3B.

Similarly to the process described above with respect to FIGS. 2A-2C, the bonding system [50] is exposed to heat to cause the shrink wrap member [225] to contract and then to cause the adhesive member [230] to become flowable and disperse into the voids in the mesh structures [220] and [250]. The adhesive then makes contact with the wall of the first and second balloons [215] and [245], thereby bonding the mesh structures to the first and second balloons. In some cases, the continued exposure to temperature and/or dynamic pressure exerted by the contracting shrink wrap member [225] causes the adhesive [230] to make contact with the wall of the catheter shaft [210]. The resulting composite structure [240] illustrated in FIG. 3B bonds the balloons, the mesh and the catheter shaft together, thereby providing a low profile, very durable bonding mechanism. The composite structure [240] also fills any spaces, i.e. [240], between the two balloons to provide a uniform bonding surface structure.

Those skilled in the art will recognize that the bonding system and method of the present invention provides for a uniform pressure-flow of hot-melt adhesive and simultaneous containment of the adhesive that solves one of the most common problems with hot-melt adhesives, that being adhesive "web/thread" formation at the point where traditional hot-melts are stopped being dispensed. This web/thread is both a cleanliness and cosmetic issue that is overcome by the current invention. Additionally, those skilled in the art will recognize that the containment function of the shrink wrap member provides means to ensure that only the areas desired to be covered by the adhesive are controlled more effectively than through means of typical traditional manual hot-gun application of hot-melt adhesives, which simultaneously overcomes through elimination of the step of adhesive shaping traditionally performed with hot-melt type adhesive dispensers.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for bonding a porous structure to at least one other structure, comprising:
    a catheter, wherein the catheter has a first inflatable balloon positioned at the distal end of the catheter and having a first balloon mesh structure positioned over at least a portion of the first balloon and a second inflatable balloon positioned proximally of the first balloon and having a second balloon mesh structure positioned over at least a portion of the second balloon,
    an inner adhesive member positioned over at least a portion of the first balloon mesh structure and at least a portion of the second balloon mesh structure, the inner adhesive member having a melting temperature;
    an outer shrink wrap member positioned over and at least partially enclosing the inner adhesive member, the outer shrink wrap member having a recovery temperature;
    wherein the melting temperature is higher than the recovery temperature.

2. The bonding system of claim 1, wherein upon reaching the melting temperature, the inner adhesive member disperses into voids in the first balloon mesh structure and the second balloon mesh structure to bond the mesh structures to the first and second balloons.

3. The bonding system of claim 1, wherein the melting temperature is higher than the recovery temperature by at least about ten degrees Fahrenheit.

4. The bonding system of claim 1, wherein the inner adhesive member comprises a polyolefin.

5. The bonding system of claim 1, wherein the inner adhesive member comprises a maleic anhydride modified ethylene-vinyl acetate copolymer.

6. The bonding system of claim 1, wherein the outer shrink wrap member comprises a polyolefin.

7. The bonding system of claim 1, wherein the outer shrink wrap member comprises a polyethylene.

8. The bonding system of claim 1, wherein the outer shrink wrap member comprises at least one weakened zone such that the outer shrink wrap member is adapted to be torn along the weakened zone and removed.

9. The bonding system of claim 1, wherein the inner adhesive member is at least partially fixated inside the outer shrink wrap member prior to positioning the inner adhesive member over at least a portion of the first balloon mesh structure and at least a portion of the second balloon mesh structure.

10. The bonding system of claim 1, wherein the inner adhesive member has a cylindrical shape with an outer diameter.

11. The bonding system of claim 10, wherein the outer shrink wrap member has a cylindrical shape with an inner diameter that is slightly larger than the outer diameter of the inner adhesive member such that the inner member is accommodated inside the outer member.

12. The bonding system of claim 1, wherein the outer shrink wrap member exerts pressure on the inner adhesive member upon reaching the recovery temperature, and wherein the inner adhesive member disperses into voids in the mesh structures to bond the mesh structures to the inflatable balloons upon reaching the melting temperature.

13. The bonding system of claim 12, wherein the inner adhesive member comes into contact with an elongated shaft of the catheter and bonds the mesh structures and the inflatable balloons to the elongated shaft.

* * * * *